US006841561B1

(12) United States Patent
Tan et al.

(10) Patent No.: US 6,841,561 B1
(45) Date of Patent: Jan. 11, 2005

(54) DIHYDROOROTATE DEHYDROGENASE INHIBITORS FOR THE TREATMENT OF VIRAL-MEDIATED DISEASES

(75) Inventors: Yin Hwee Tan, Singapore (SG); John Stanford Driscoll, Rockville, MD (US); Sim Mui Mui, Singapore (SG)

(73) Assignee: Institute of Molecular and Cell Biology, Singapore (SG)

( * ) Notice: Subject to any disclaimer, the term of this patent is extended or adjusted under 35 U.S.C. 154(b) by 0 days.

(21) Appl. No.: 10/089,553

(22) PCT Filed: Sep. 29, 2000

(86) PCT No.: PCT/US00/26797

§ 371 (c)(1),
(2), (4) Date: May 8, 2002

(87) PCT Pub. No.: WO01/24785

PCT Pub. Date: Apr. 12, 2001

Related U.S. Application Data

(60) Provisional application No. 60/157,017, filed on Oct. 1, 1999.

(51) Int. Cl.[7] ...................... A61K 31/47; C07D 215/02; C07D 215/16; C07D 215/20
(52) U.S. Cl. ........................ 514/311; 546/165; 546/170; 546/178
(58) Field of Search ........................ 514/311; 546/165, 546/170, 178

(56) References Cited

U.S. PATENT DOCUMENTS 4,680,299 A 7/1987 Hesson

FOREIGN PATENT DOCUMENTS

| EP | 0 601 191 | 6/1994 |
| EP | 0 721 942 | 7/1996 |
| WO | WO 2000054003 | * 8/2000 |
| WO | WO 2002053138 | * 7/2002 |

OTHER PUBLICATIONS

Nakazato Yoshisuke, "Tetracyclic Quinoline Derivative", Patent Abstracts of Japan, vol. 1998, No. 14, Dec. 31, 1998.

* cited by examiner

*Primary Examiner*—D. Margaret Seaman
(74) *Attorney, Agent, or Firm*—Nixon & Vanderhye P.C.

(57) ABSTRACT

Flavivirus, rhabdovirus and paramyxovirus infections may be treated by administering an inhibitor of the enzyme dihydroorotate dehydrogenase such as 6-fluoro-2-(2'-fluoro-1,1'-biphenyl-4-yl)-3-methyl-4-quinolinearcarboxylic acid sodium salt (Brequinar). A synergistic effect can be obtained if an interferon such as interferon α2, interferon α8 or interferon β, or an inhibitor of a second enzyme selected from inosine monophosphate dehydrogenase, guanosine monophosphate synthetase, cytidine triphosphate synthetase and S-adenosylhomocysteine hydrolase, is also administered.

23 Claims, No Drawings

DIHYDROOROTATE DEHYDROGENASE INHIBITORS FOR THE TREATMENT OF VIRAL-MEDIATED DISEASES

This application is a 371 of International Application No. PCT/US00/26797, filed Sep. 29, 2000, which claims priority from Provisional Application No. 60/157,017, filed Oct. 1, 1999, the entire content of which is incorporated herein by reference.

FIELD OF THE INVENTION

This invention relates to the treatment of infections caused by viruses of the Flaviviridae, Rhabdoviridae and Paramyxoviridae families.

BACKGROUND TO THE INVENTION

At present there is no effective treatment for chronic hepatitis C. So far, human interferons have been used to treat patients with chronic hepatitis C. The efficacy of this treatment is about 20%. Recently, Ribavirin has been used in combination with interferon to treat patients with chronic hepatitis C. The combined treatment efficacy is up to about 40%. However, the dosage of Ribavirin required is high and there is accompanying red blood cell toxicity.

The search for effective drug(s) for hepatitis C is under the scrutiny of investigators worldwide. Most if not all the enzymes of hepatitis C and related viruses of the Flaviviridae family have been used as targets in the search for an antiviral drugs against hepatitis C. A major problem with the study of hepatitis C is a lack of in vitro cell-based and animal model systems. To date, there is no good replicative cell system to assay for activity against hepatitis C virus. The only animal model for hepatitis C is the chimpanzee. However, chronic hepatitis C infection is difficult to establish in chimpanzees. This fact further complicates the use of chimpanzees as an animal model system.

SUMMARY OF THE INVENTION

"Surrogate" virus/host cell systems were used to search for antiviral compounds which can be used as antiviral drugs to treat patients with acute and chronic hepatitis C in particular, and flavivirus, rhabdovirus and paramyxovirus infections in general. Several families of compounds which are structural and biological analogues were selected for testing for their antiviral activities in human and monkey cells against three viruses of the Flaviviridae family (yellow fever, kunjin and dengue viruses), a virus of the Rhabdoviridae family (vesicular stomatitis virus; VSV) and a virus of the Paramyxoviridae family (respiratory syncytial virus; RSV). These are all RNA viruses that infect human and non-human primate cells.

It was found that the 6-fluoro-2-(2'-fluoro-1,1'-biphenyl-4-yl)-3-methyl-4'-quinolinecarboxylic acid sodium salt (Brequinar) and other inhibitors of the enzyme dihydroorotate dehydrogenase exhibited potent activity against the viruses tested. Ribavirin was also tested. The dihydroorotate dehydrogenase inhibitors were always more potent than, and indeed act synergistically in combination with, an interferon. An inhibitor of dihydroorotate dehydrogenase can also be administered in combination therapy with an inhibitor of a second enzyme selected from inosine monophosphate dehydrogenase, guanosine monophosphate synthetase, cytidine triphosphate synthetase and S-adenosylhomocysteine hydrolase, optionally in further combination with an interferon, to provide a synergistic antiviral effect.

Accordingly, the present invention provides a method of treating a host infected with a virus of the Flaviviridae, Rhaboviridae or Paramyxoviridae family, which method comprises the step of administering to the host an inhibitor of dihydroorotate dehydrogenase.

The invention additionally provides:

novel compounds which are structural rogues of Brequinar and their preparation;

use of an inhibitor of dihydroorotate dehydrogenase in the manufacture of a medicament for use in the treatment of an infection attributable to a virus of the Flaviviridae, Rhabdoviridae, or Paramyxoviridae family;

an anti-flavivirus agent, anti-rhabdovirus or anti-paramyxovirus agent comprising an inhibitor of dihydroorotate dehydrogenase;

products containing an inhibitor of dihydroorotate dehydrogenase and an interferon as a combined preparation for simultaneous, separate or sequential use in treating an infection attributable to a virus of the Flaviviridae, Rhabdoviridae or Paramyxoviridae family;

products containing an inhibitor of dihydroorotate dehydrogenase and an inhibitor of a second enzyme selected from inosine monophosphate dehydrogenase, guanosine monophosphate synthetase, cytidine triphosphate synthetase and S-adenosylhomocysteine hydrolase as a combined preparation for simultaneous, separate or sequential use in treating an infection attributable to a virus of the Flaviviridae, Rhabdoviridae or Paramyxoviridae family; and A method for identifying an anti-flavivirus, anti-rhabdovirus or anti-paramyxovirus agent, which method comprises testing a test compound for its ability to inhibit dihydroorotate dehydrogenase.

DETAILED DESCRIPTION OF THE INVENTION

Inhibitors of Dihydroorotate Dehydrogenase

Dihydroorotate dehydrogenase (DHO-DH, DHOD, EC 1.3.3.1) is the fourth enzyme in the de novo pyrimidine biosynthetic pathway. Any inhibitor of this enzyme is used in the present invention.

A technique for identifying inhibitors of dihydroorotate dehydrogenase using a computer algorithm is described in Biochemical and Biophysical Research Communications 223, 654–659 (1996) and in Biochemical Pharmacology vol 49, No. 7, pp 947–954 (1995). The technique involves the correlation of the biological activity of a given compound with the biological activity of known DHOD inhibitors such as dichloroallyl lawsone and Brequinar. The COMPARE computer algorithm may be used for the correlation (see J. Natl. Cancer Inst. 81, 1088–1092, 1989).

An in vitro assay for inhibitors of mouse liver dihydroorotate dehydrogenase is described in J. Biol. Chem. 270, No. 38, pages 22467–22472 (1995). Mouse liver dihydroorotate dehydrogenase may be prepared as described in Biochem. J. (1998), 336, 299–303 (1998).

Inhibitors of dihydroorotate dehydrogenase are described, for example, by Douglas G. Batt in Exp. Opin. Ther. Patents (1999)9(1), 41–54, the contents of which are incorporated herein by reference.

The fact that inhibitors of dihydroorotate dehydrogenase have been found to have activity against certain classes of RNA virus offers a means of screening for new antiviral agents. Accordingly the invention provides a method ofor identifying an anti-flavivirus, anti-rhabdovirus or anti-paramyxovirus agent, which method comprises:

(a) providing a test compound;
(b) d whether the test compound has activity as an inhibitor of dihydroorotate dehydrogenase; and
(c) selecting the test compound as an anti-flavivirus, anti-rhabdovirus or anti-paramyxovirus agent if it is shown to have activity in step (b).

The candidate test compounds may be tested for dihydroorotate dehydrogenase inhibitory activity by any known technique, such as those mentioned above.

Four classes of dihydroorotate dehydrogenase inhibitors are preferred for use in the present invention. These are:

compounds of the formula (I):

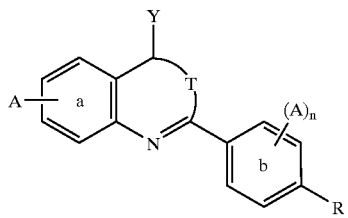

(I)

wherein:

each A is independently selected from the group consisting of hydrogen, halogen, perhaloalkoxy, amino $C_1$–$C_8$ alkyl, $NO_2$, CN, $SO_2CH_3$. $C_1$–$C_8$ alkyl, $C_1$–$C_8$ alkoxy, $C_3$–$C_7$ cycloalkyl, $C_3$–$C_7$ cycloalkenyl, aryl, aryloxy, $C_1$–$C_6$ perhaloalkyl and Y; or two adjacent groups A on ring b form, together with the phenyl ring to which they are attached, a naphthalene ring system;

R is cyclohexyl, phenoxy or benzoxy, or a phenyl ring which is unsubstituted or substituted by a group A as defined above; or R and an adjacent group A on ring b form, together with the phenyl ring to which they are attached, a naphthalene or phenanthrene ring system;

Y is selected from the group consisting of COOM, CONHR', $SO_3M$ and hydrogen;

M is selected from the group consisting of H, Li, Na, K and 0.5 Ca;

R' is $C_1$–$C_{10}$ alkyl;

n is 1 or 2; and

T is =N— or =C(Z)— wherein either:
(i) Z is selected from the group consisting of hydrogen, $NH_2$, OH, $C_1$–$C_8$ alkyl, $C_3$–$C_7$ cycloalkyl, aryl and $C_1$–$C_6$ perhaloalkyl, or
(ii) Z is a bridging moiety selected from the group consisting of —V—W— (wherein V is $CH_2$ or S and W is $CH_2$, O, S or NH) and —$(CH_2)_2$—C(=Z)— wherein Z is O or $H_2$, the said bridging moiety being attached to the ortho position of ring b of the adjacent biphenyl group, thereby completing a ring;

compounds of formula (I'):

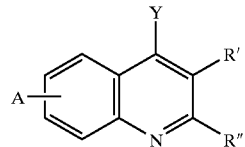

(I')

wherein A and Y are as defined above for formula (I);
R' is hydrogen and R" is a thiophene ring or a group of formula (i') or (ii'):

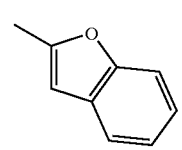

(i')

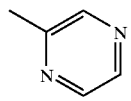

(ii')

or R' and R" form, together with the carbon atoms (denoted "C") to which they are attached, a ring system of formula (iii') or (iv'):

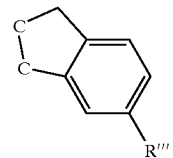

(iii')

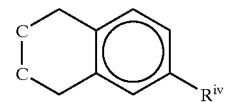

(iv')

wherein R''' is H or halogen and $R^{iv}$ is H or $C_1$–$C_6$ alkoxy;
compounds of formula (III):

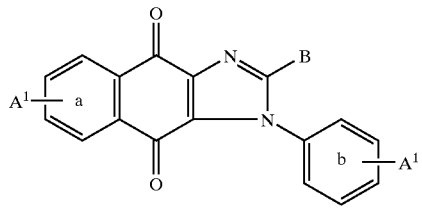

(III)

wherein:
each $A^1$ is independently selected from the group consisting of hydrogen, $C_1$–$C_8$ alkyl, $C_1$–$C_8$ alkoxy, $C_2$–$C_8$ alkenyl, $C_2$–$C_8$ alkynyl, $C_3$–$C_7$ cycloalkyl, halogen, unsubstituted amyl, X-substituted aryl, $NO_2$, CN, COOR, CONHR and NHR;
X is selected from the group consisting of halogen, $NO_2$, $C_1$–$C_8$ alkyl, aryl, fused aryl and COOR;
R is selected from the group consisting of hydrogen and $C_1$–$C_8$ alkyl; and B is selected from the group consisting of $C_1$–$C_8$ ally, H, $CF_3$ and aryl which is unsubstituted or substituted by halogen, $C_1$–$C_8$ alkoxy, $C_1$–$C_8$ alkyl, $NO_2$, aryl or fused aryl;

compounds of the formula (V):

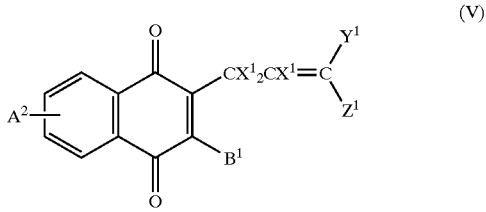

(V)

wherein:
$A^2$ is selected from the group consisting of hydrogen, $C_1$–$C_8$ alkyl, $C_2$–$C_8$ alkenyl, $C_2$–$C_8$ alkynyl, $C_3$–$C_7$ cycloalkyl, halogen, unsubstituted aryl, halogen-substituted aryl, fused aryl, $NO_2$, CN, $NHR^1$ and $N(R^1)_2$;

$R^1$ is selected from the group consisting of hydrogen, $C_1$–$C_8$ alkyl and OH;

$X^1$ is hydrogen or halogen; and $B^1$, $Y^1$ and $Z^1$ are each independently selected from hydrogen, OH, $C_1$–$C_8$ alkyl, halogen, CN, $NO_2$ and $CF_3$; and compounds of the formula (VII):

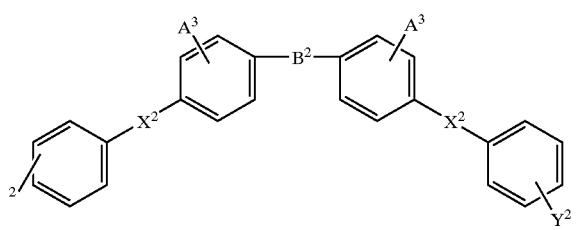

(VII)

wherein:
each $A^3$ is independently selected from the group consisting of hydrogen, $C_1$–$C_8$ alkyl, $C_1$–$C_{10}$ alkoxy, halogen and $N(R^2)_2$;

$B^2$ is a direct bond, —CH=CH— or —C≡C—;

$X^2$ is selected from the group consisting of O, S and $NR^2$;

$R^2$ is selected from the group consisting of hydrogen, $C_1$–$C_4$ alkyl and aryl;

$Y^2$ is selected from the group consisting of $COOM^1$ and $SO_3M^1$; and $M^1$ is selected from the group consisting of H, Li, Na, K and 0.5 Ca.

A halogen atom may be fluoro, chloro, bromo or iodo. A $C_1$–$C_8$ alkyl group is suitably a $C_1$–$C_4$ alkyl group. A $C_1$–$C_4$ alkyl group is typically methyl, ethyl, n-propyl, isopropyl or butyl. A $C_3$–$C_7$ cycloalkenyl group is typically cyclohexenyl. A $C_3$–$C_7$ cycloalkyl group is typically a cyclopentyl or cyclohexyl group. A $C_1$–$C_6$ perhaloalkyl group may be a $C_1$–$C_4$ perhaloalkyl group. The halo atom may be chloro or fluoro. A particularly suitable perhaloalkyl group is trifluoromethyl.

An aryl group is typically a phenyl. A $C_2$–$C_8$ alkenyl group is suitably a $C_2$–$C_4$ alkenyl group. A $C_2$–$C_8$ alkynyl group is suitably a $C_2$–$C_4$ alkynyl group. Fused aryl is generally naphthyl. A $C_1$–$C_{10}$ alkoxy group is preferably a $C_1$–$C_6$ alkoxy group, for example a $C_1$–$C_4$ alkoxy group such as methoxy or ethoxy.

Perhaloalkoxy is, for example, $OCF_3$, $OCCl_3$ or $OCBr_3$. Preferably it is $OCF_3$. Aryloxy is, for example, phenoxy or benzyloxy.

The compounds of formula (I) are known and may be prepared by published methods or by submitting compounds produced by the published methods to routine synthetic modifications and interconversion which are well known inorganic chemistry. Literature references for many of the published methods are quoted in the paper by Douglas G. Batt cited above. For instance, compounds of formula (I) in which T is =C(Z)— may be prepared as described in U.S. Pat. No. 4,680,299. Compounds of formula (I) in which T is =N— may be prepared as described in U.S. Pat. No. 4,639,454. Compounds of formula (I) in which Z is a bridging moiety as defined above may be prepared as described in U.S. Pat. No. 4,918,077, U.S. Pat. No. 5,002,954, WO9506640, U.S. Pat. No. 5,371,225, EP-A-721942, JP10231289, Organ Biol. (1997)4(2): 43–48 and 49–57, JP-6306079-A2 and $216^{th}$ ACS Meeting, Boston USA (1998) ORGN 132. Compounds of formula (I') may be prepared using the same synthetic strategy as that described in U.S. Pat. No. 4,680,299.

Preferred compounds of formula (I) are those in which:
each A is independently selected from the group consisting of hydrogen, halogen (preferably F) amino $C_1$–$C_8$ alkyl (preferably $NH_2(CH_2)$—), $C_1$–$C_8$ alkyl (preferably $CH_3$) and $C_1$–$C_6$ perhaloalkyl (preferably $CF_3$);

Y is selected from the group consisting of COOM and CONHR' wherein M is as defined above and R' is $C_5$–$C_{10}$ alkyl, preferably octyl;

T is =C(Z)— wherein
(i) Z is selected from the group consisting of hydrogen, $C_1$–$C_8$ alkyl (preferably $CH_3$), $NH_2$ and OH, or
(ii) Z is a bridging moiety as defined above selected from the group consisting of —$(CH_2)$—, —$(CH_2)_3$—, —$SCH_2$—, —$CH_2O$—, —$CH_2S$—, —$CH_2NH$— and —$(CH_2)$—C(=O)—.

In formula (I) the substituent A in ring a is preferably $OCF_3$, halogen (most preferably F) or $NH_2(CH_2)_2$—, preferably bonded at position 6 of the quinoline ring system. The substituent A in ring b is preferably hydrogen.

Examples of compounds of formula (I) include those of formula (Ia):

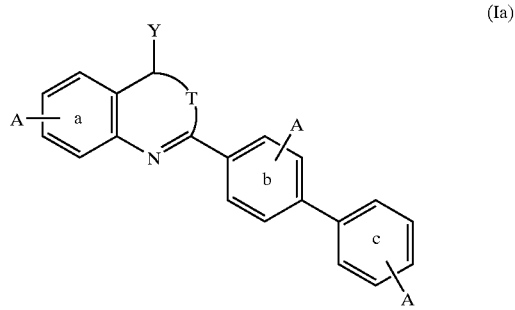

(Ia)

wherein:
each A is independently selected from the group consisting of hydrogen, halogen, amino $C_1$–$C_8$ alkyl, $NO_2$, CN, $SO_2CH_3$, $C_1$–$C_8$ alkyl, $C_3$–$C_7$ cycloalkyl, aryl, $C_1$–$C_6$ perhaloalkyl and Y;

Y is selected from the group consisting of COOM, CONHR' SO₃M and hydrogen;

M is selected from the group consisting of H, Li, Na, K and 0.5 Ca;

R' is $C_1$–$C_{10}$ alkyl; and

T is =N— or =C(Z)— wherein either:
(i) Z is selected from the group consisting of hydrogen, $NH_2$, OH, $C_1$–$C_8$ alkyl, $C_3$–$C_7$ cycloalkyl aryl and $C_1$–$C_6$ perhaloalkyl, or
(ii) Z is a bridging moiety selected from the group consisting of —V—W— (wherein V is $CH_2$ or S and W is $CH_2$, O, S or NH) and —$(CH_2)_2$13 C(=Z)— wherein Z is O or $H_2$, the said bridging moiety being attached to the ortho position of ring b of the adjacent biphenyl group, thereby completing a ring.

The substituent A in ring c of formula (Ia) is preferably hydrogen or ortho-halogen (most preferably ortho-F).

Amongst preferred compounds of formula (I) are those of formula (II):

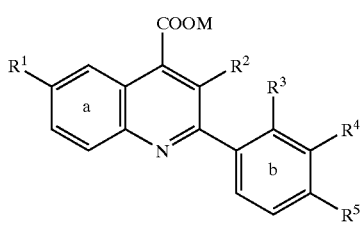

(II)

wherein $R^1$ is H, a halogen or $OCF_3$;

M is as defined above;

$R^2$ is H or $C_1$–$C_6$ alkyl;

$R^3$ is H or $OR^6$ wherein $R^6$ is H or $C_1$–$C_6$ alkyl;

$R^4$ is H or $C_1$–$C_6$ alkyl; or $R^3$ and $R^4$ form, together with phenyl ring b to which they are attached, a naphthalene ring; and $R^5$ is cyclohexyl, phenoxy or benzoxy, or a phenyl ring which is unsubstituted or substitued by halogen; or $R^4$ and $R^5$ form, together with phenyl ring b to which they are attached, a phenanthrene ring.

Substitution patterns of specific compounds of formula (II) are as follows:

| $R^1$ | M | $R^2$ | $R^3$ | $R^4$ | $R^5$ | Compound |
|---|---|---|---|---|---|---|
| F | H | $CH_3$ | H | H | 2-fluorophenyl | Brequinar |
| F | H | H | H | H | phenyl | I3K5 |
| F | H | $CH_3$ | H | H | phenyl | I3K55 |
| F | H | H | H | H | cyclohexyl | I3K46 |
| F | H | H | H | H | phenoxy | I3K52 |
| F | H | H | OH | $CH_3$ | benzoxy | I3K53 |
| H | H | H | H | H | phenoxy | I1K52 |
| H | H | H | H | H | cyclohexyl | I1K46 |
| H | H | H | OH | $CH_3$ | benzoxy | I1K53 |
| H | H | $CH_3$ | H | H | phenyl | I1K55 |
| $OCF_3$ | H | H | H | H | phenyl | I2K5 |
| F | H | H | H | form with ring b a phenanthrene ring of formula: | | I3K4 |

-continued

| $R^1$ | M | $R^2$ | $R^3$ | $R^4$ | $R^5$ | Compound |
|---|---|---|---|---|---|---|
| F | H | H | form with ring b a naphthalene ring | | F | I3K36 |
| $OCF_3$ | H | H | H | H | cyclohexyl | I2K46 |
| $OCF_3$ | H | $CH_3$ | H | H | phenyl | I2K55 |
| $OCF_3$ | H | H | $OCH_3$ | $CH_3$ | benzoxy | I2K51 |
| $OCF_3$ | H | H | H | H | phenoxy | I2K52 |
| F | H | H | $OCH_3$ | $CH_3$ | benzoxy | I3K51 |
| F | H | H | form with ring b a naphthalene ring | | H | I3K6 |

Especially preferred is the sodium salt of Brequinar, which has the formula (IIb):

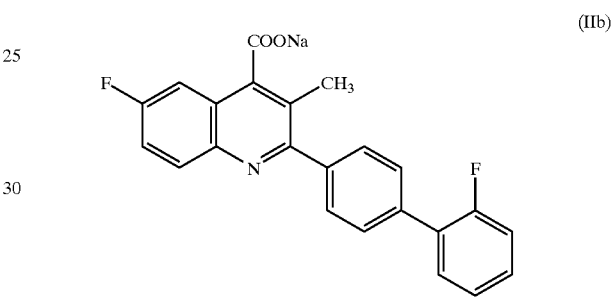

(IIb)

Brequinar can be prepared as described in U.S. Pat. No. 4,680,299 (Example 28).

Some of the compounds of formula (II) are novel. Accordingly, the invention further provides a compound of formula (IIa)

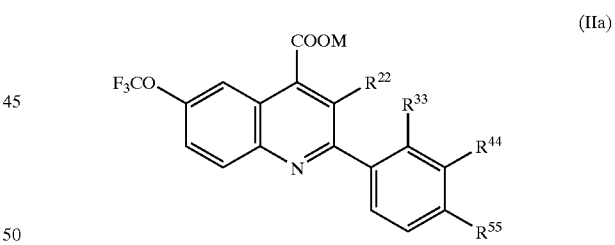

(IIa)

wherein

M is selected from the group consisting of H, Li, Na, K and 0.5 Ca;

$R^{22}$ is H or $C_1$–$C_6$ alkyl;

$R^{33}$ is H or $OR^6$ wherein $R^6$ is H or $C_1$–$C_6$ alkyl;

$R^{44}$ is H or $C_1$–$C_6$ alkyl; and $R^{55}$ is phenyl, cyclohexyl, phenoxy or benzoxy.

Preferred examples of the compounds of formula (IIa) are:

2-(4-biphenylyl)-6-trifluoromethoxy-quinoline-4-carboxylic acid (compound I2K5);

2-(4-biphenylyl)-3-methyl-6-trifluoromethoxy-quinoline-4-carboxylic acid (compound I2K55);

2-(4-cyclohexylphenyl)-6-trifluoromethoxy-quinoline-4-carboxylic acid (compound I2K46);

2-(4-benzyloxy-2-methoxy-3-methyl-phenyl)-6-trifluoromethoxy-quinoline-4-carboxylic acid (compound I2K51); and 2-(4-phenoxyphenyl)-6-trifluoromethoxy-quinoline-4-carboxylic acid (compound I2K52).

The compounds of formula (II), including the novel compounds of formula (IIa), may be prepared by the synthetic route described in U.S. Pat. No. 4,680,299 mentioned above. This involves the Pfitzinger reaction, whereby an appropriately substituted isatin is condensed with an appropriately substituted ketone (J. Org. Chem. 18, 1209, 1953).

Accordingly, the invention further provides a process for producing a compound of formula (IIa) as defined above, which process comprises a) condensing the trifluoromethoxy-substituted isatin compound of the following formula (IX):

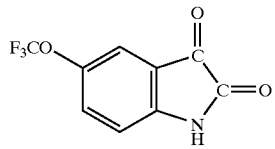

(IX)

with a ketone of formula (X):

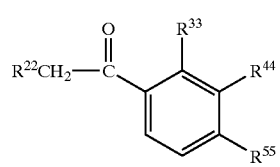

(X)

wherein $R^{22}$, $R^{33}$, $R^{44}$ and $R^{55}$ are as defined above for formula (IIa), in the presence of a base; and (b) if desired, converting a resulting compound of formula (IIa) in which M is H into a pharmaceutically acceptable salt thereof wherein M is Li, Na, K or 0.5 Ca.

The base used in step (a) may be an inorganic base or an organic base. Preferred bases include potassium hydroxide and sodium hydroxide. The reaction is generally conducted in a solvent. The solvent is preferably ethanol.

Preferred compounds of formula (I') have the following substitution patterns:

| A | Y | R' | R" | Compound |
|---|---|---|---|---|
| 6-F | COOH | H | formula (i') | I3K44 |
| 6-OCF$_3$ | COOH | formula (iv') wherein $R^{iv}$ is methoxy | | I2K42 |
| 6-OCF$_3$ | COOH | formula (iii') wherein $R^{iii}$ is F | | I2K43 |
| 6-F | COOH | formula (iv') wherein $R^{iv}$ is methoxy | | I3K42 |
| 6-OCF$_3$ | COOH | CH$_3$ | thiophen-2-yl | I2K20 |
| 6-F | COOH | formula (iii') wherein $R^{iii}$ is F | | I3K43 |
| H | COOH | H | formula (i') | I1K44 |

Preferred compounds of formula (III) are those in which:

each $A^1$ is independently selected from the group consisting of hydrogen, halogen, $C_1$–$C_8$ alkyl and $C_1$–$C_8$ alkoxy; and B is selected from the group consisting of hydrogen, $C_1$–$C_8$ alkyl, phenyl and benzyl, the said phenyl and benzyl being unsubstituted or substituted by halogen (preferably Cl or Br), $C_1$–$C_8$ alkoxy (preferably $C_1$–$C_4$ alkoxy such as OCH$_3$) or $C_1$–$C_8$ alkyl (preferably $C_1$–$C_4$ alkyl such as CH$_3$).

When B is substituted phenyl or benzyl as defined above, the substituent is preferably at position 4 of the phenyl ring. The group $A^1$ in ring a is preferably H. The group $A^1$ in ring b is preferably H, or it is para-$C_1$–$C_8$ alkoxy or para-halogen (preferably Cl or Br).

Especially preferred is 1-(p-bromophenyl)-2-methyl-1H-naphth[2,3-d]imidazole-4,9-dione (BNID) which has the formula (IV):

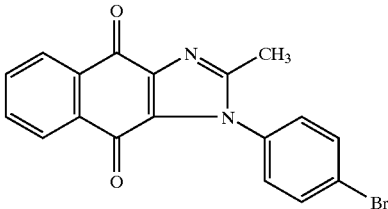

(IV)

The compounds of formula (III) may be prepared as described in J. Med. Chem. 1996, 39, 1447–1451, or by submitting compounds produced as described in this document to routine synthetic modifications and interconversion which are well known in organic chemistry. BNID can be prepared as described in J. Med. Chem. 1964, 7, 362–364.

Preferred compounds of formula (V) are those in which $A^2$ is selected from the group consisting of hydrogen, $C_1$–$C_8$ alkyl (preferably $C_1$–$C_4$ alkyl such as CH$_3$) and halogen;

B is hydrogen or OH;

$X^1$ is hydrogen; and $Y^1$ and $Z^1$ are each independently selected from the group consisting of hydrogen, halogen (preferably Cl) and $C_1$–$C_8$ alkyl (preferably $C_1$–$C_4$ alkyl such as CH$_3$).

Especially preferred is dichloroallyl lawsone which has the formula (VI):

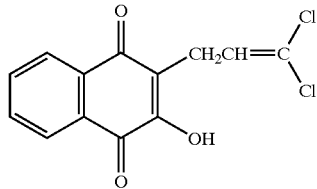

(VI)

The compounds of formula (V) may be prepared as described in U.S. Pat. No. 3,655,699 or WO9106863, or by submitting compounds produced as described in these documents to routine synthetic modifications and interconversions which are well known in organic chemistry. Dichloroallyl lawsone can be prepared as described in U.S. Pat. No. 3,655,699.

Preferred compounds of formula (VII) are those in which each $A^3$ is hydrogen or $C_1$–$C_{10}$ alkoxy (preferably $C_1$–$C_6$ alkoxy such as methoxy);

$B^2$ is a direct bond;

$X^2$ is $NR^2$ wherein $R^2$ is hydrogen or $C_1$–$C_4$ alkyl; and $Y^2$ is COOH.

Preferably each $A^3$ in formula (VII) is positioned meta to the linking group $B^2$, and each $Y^2$ is positioned ortho to the linking group $X^2$.

Especially preferred is 2,2'-[3,3'-dimethoxy[1,1'-biphenyl]-4,4'-diyl)diimino]bis-benzoic acid (redoxal) which has the formula (VIII):

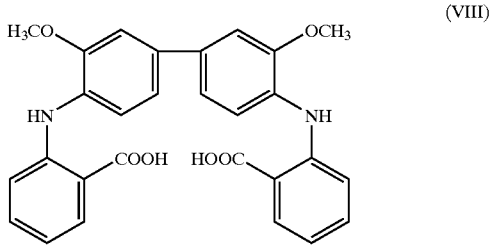

(VIII)

Redoxal is described in Zhur. Anal. Khim. 15, pp 671–475, 1960 and Chemical Abstracts 1961 vol. 5, 18447b. Other compounds of formula (VII) may be prepared by routine synthetic modifications and interconversion of compounds prepared in this reference.

Interferons

The interferon for use in the present invention may be an interferon α, such as interferon α2 or α8, or interferon β. The term "interferon" includes fragments which have interferon activity and mutant forms of an interferon which retain interferon activity. For example, the sequence of an interferon α or β may have been modified to enhance activity or stability as reported in U.S. Pat. No. 5,582,824, U.S. Pat. No. 5,593,667 or U.S. Pat. No. 5,594,107.

The interferon may have been purified from natural sources or may be a recombinant interferon. The species of interferon is generally the same as the host species to which the interferon is administered. The invention is particularly applicable to the treatment of flavivirus infections in humans. Preferably therefore a human interferon such as human interferon α2 or α8 or human interferon β is used.

The interferon α8, particularly the human interferon α8, typically has a specific activity of more than $0.3 \times 10^9$, generally from $0.3 \times 10^9$ to $3 \times 10^9$ and preferably from $0.5 \times 10^9$ to $3 \times 10^9$, IU per mg protein. The human interferon β typically has a specific activity of from $4 \times 10^8$ to $8 \times 10^8$, preferably from $4.8 \times 10^8$ to $6.4 \times 10^8$, IU per mg protein. Interferon a and interferon β specific activities are determined according to reference standards MRC 69/19 and Gb-23-902-531 respectively. Specific activity is determined according to a modification of the method of Armstrong, Applied Microbiology 21, 723, 1971, in which 0.2 μg/ml of actinomycin D is included in the viral challenge and the viral induced cytopathic effect is read directly.

The interferon such as the interferon α2 or α8 or the interferon β is preferably obtainable by the methodology of WO 96/30531. The interferon is thus obtainable by a process comprising culturing mammalian cells transfected with a nucleic acid vector comprising:

(i) a coding sequence which encodes the interferon and which is operably linked to a promoter capable of directing expression of the coding sequence in mammalian cells in the presence of a heavy metal ion;

(ii) a first selectable marker sequence which comprises a metallothionein gene and which is operably linked to a promoter capable of directing expression of the metallothionein gene in the cells in the presence of a heavy metal ion; and (iii) a second selectable marker sequence which comprises a neo gene and which is operably linked to a promoter capable of directing expression of the neo gene in the cells;

unless conditions that allow expression of the coding sequence; and recovering the interferon thus produced.

The transfected mammalian cells may be cells of a human or animal cell line. They may be BHK, COS, Vero, human fibroblastoid such as ClO, HeLa, or human lymphoblastoid cells or cells of a human tumour cell line. Preferably, however, the cells are CHO cells, particularly wild-type CHO cells.

Desirably, transfected cells will have all or part of such a vector integrated into their genomes. Such cells are preferred because they give stable expression of the coding sequence contained in the vector. Preferably, one or more copies of the entire vector will be integrated, with cells having multiple integrated copies of the vector, for example from 20 to 100 copies or more, being particularly preferred because these cells give a high stable level of expression of the coding sequence contained in the vector.

However, cells having less than complete sections of the vectors integrated into their genomes can be employed if they are functionally equivalent to cells having the entire vector integrated into their genomes, in the sense that the integrated sections of the vector enable the cell to express the coding sequence and to be selected for by the use of heavy metals. Thus, cells exhibiting partial integration of a vector may be employed if the integrated element or elements include the coding sequence operably linked to its associated promoter and the metallothionein marker sequence operably linked to its associated promoter.

Any promoter capable of enhancing expression in a mammalian cell in the presence of a heavy metal ion such as $Cd^{2+}$, $Cu^{2+}$ and $Zn^{2+}$ may be operably linked to the interferon coding sequence. A suitable promoter is a metallothionein gene promoter. The mouse metallothionein gene I (mMT1) promoter is preferred.

Suitable promoter/enhancer combinations for the coding sequence include the mMT1 promoter flanked upstream with a mouse sarcoma virus (MSV) enhancer (MSV-mMT1) and a Rous sarcoma virus (RSV) enhancer upstream of a mouse mammary tumour virus (MMTV) promoter. MSV-mMT1 is preferred.

As far as the first selectable marker sequence is concerned, any promoter capable of enhancing expression in a mammalian cell in the presence of a heavy metal ion such as $Cd^{2+}$, $Cu^{2+}$ and $Zn^{2+}$ may be operably linked to the metallothionein gene such as a human metallothionein gene. Preferably, the marker sequence gene is a human metallothionein gene, such as the human metallothionein gene IIA, which has its own promoter.

The second selectable marker sequence is a neo gene. More than one type of this gene exists in nature: any specific neo gene can be used in a vector of the invention. One preferred neo gene is the E.coli neo gene.

The promoter for the neo gene is capable of directing expression of the gene in a mammalian cell. Suitable promoters are the cytomegalovirus (CMV) early promoter, the SV40 promoter, the mouse mammary tumour virus promoter, the human elongation factor 1 α-P promoter (EF-1α-P), the SRα promoter and a metallothionein gene promoter such as mMT1. The promoter may also be capable of expressing the neo gene in bacteria such as E.coli in which a vector may be constructed.

The interferon coding sequence (i) and the marker sequences (ii) and (iii) are thus each operably linked to a promoter capable of directing expression of the relevant sequence. The term "operably linked" refers to a juxtaposition wherein the promoter and the coding/marker sequence are in a relationship permitting the coding/marker sequence to be expressed under the control of the promoter. Thus, there may be elements such as 5' non-coding sequence between the promoter and coding/marker sequence. Such sequences can be included in the construct if they enhance or do not impair the correct control of the coding/marker sequence by the promoter.

The vector may be a DNA or RNA vector, preferably a DNA vector. Typically, the vector is a plasmid. Each of the sequences (i) to (iii) will typically be associated with other elements that control their expression. In relation to each sequence, the following elements are generally present, usually in a 5' to 3' arrangement: a promoter for directing expression of the sequence and optionally a regulator of the promoter, a translational start codon, the coding/marker sequence, a polyadenylation signal and a transcriptional terminator.

Further, the vector typically comprises one or more origins of replication, for example a bacterial origin of replication, such as the pBR322 origin, that allows replication in bacterial cells. Alternatively or additionally, one or more eukaxyotic origins of replication may be included in the vector so that replication is possible in, for example yeast cells and/or mammalian cells.

The vector may also comprise one or more introns or other non-coding sequences 3' or 5' to the coding sequence or to one or more of the marker sequences. Such non-coding sequences may be derived from any organism, or may be synthetic in nature. Thus, they may have any sequence. Such sequences may be included if they enhance or do not impair correct expression of the coding sequence or marker sequences.

The transfected cells are typically cultured in the presence of a heavy metal ion selected from $Cd^{2+}$, $Cu^{2+}$ and $Zn^{2+}$, particularly in an amount which is not toxic to the cells. That can lead to higher expression of the desired interferon. The concentration of the heavy metal ion in the culture medium is typically from 100 to 200 $\mu$M. Cells may therefore be cultured in the presence of from 100 to 200 $\mu$M of a heavy metal ion selected from $Cd^{2+}$, $Cu^{2+}$ and $Zn^{2+}$, for example from 130 to 170 $\mu$M of the heavy metal ion. A useful concentration is about 150 $\mu$M particularly when the heavy metal ion is $Zn^{2+}$.

The interferon that is produced may be recovered by any suitable means and the method of recovery may vary depending on, for example, the type of cells employed and the culture conditions that have been used. Desirably, the interferon produced will be purified after recovery. Substantially pure interferon can thus be obtained.

The human β-interferon provided by WO 96/30531 has a high degree of sialylation. Like natural human β-interferon produced by primary diploid human fibroblasts, it is well glycosylated. However, it has a higher bioavailability than the natural β-interferon or recombinant β-interferon produced in E.coli (betaseron).

The higher bioavailability of the β-interferon can be characterised. When $1.5 \times 10^6$ IU of the interferon is injected subcutaneously into the back of a rabbit of about 2 kg: (a) $\geq 128$ IU/ml of the interferon is detectable in the serum of the rabbit after 1 hour, and/or (b) $\geq 64$ IU/ml of the interferon is detectable in the serum of the rabbit after 5 hours.

The maximum level of interferon is typically observed after 1 hour. According to (a), therefore, 128 to 256 IU/ml such as 140 to 190 IU/ml of the interferon may be detectable in the rabbit serum after 1 hour. After 5 hours according to (b), $\geq 70$ IU/ml such as $\geq 80$ IU/ml of the interferon may be detectable in the rabbit serum. Typically according to (b), an amount of interferon in the range of 64 to 128 IU/ml such as 80 to 110 IU/ml can be detected.

Additionally or alternatively, the human interferon β can be characterised by its specific activity. It can have a specific activity from $4.8 \times 10^8$ to $6.4 \times 10^8$ IU per mg equivalent of bovine serum albumin protein, as noted above. The specific activity may be from $5 \times 10^8$ to $6 \times 10^8$, for example from $5.2 \times 10^8$ to $5.8 \times 10^8$ such as from $5.3 \times 10^8$ to $5.5 \times 10^8$, IU per mg equivalent of bovine serum albumin protein.

The human interferon β may also be characterised by one or more of the following properties:

1. The interferon β typically has an apparent molecular weight of 26,300 as determined by 15% sodium dodecyl sulphate-polyacrylamide gel electrophoresis (SDS-PAGE).
2. When injected as a neat intravenous bolus into a rabbit, the half life of the interferon is typically in the range of from 12 to 15 min such as about 13½ min. The bolus is injected into the rabbit ear vein and blood samples are withdrawn from the rabbit ear artery. Rabbit serum is assayed for the antiviral activity of the interferon according to the modification of the method of Armstrong (1971).
3. The antiviral activity of the interferon in a human hepatoblastoma cell line (HepG2) is at least equal to and, typically, about 1.5 times the activity of natural interferon β from primary diploid human fibroblast cells. The interferon is also about 2.2 times more effective than betaseron in protecting Hep2 cells against a viral challenge. Antiviral activity is again determined according to the modified method of Armstrong (1971). Actinomycin D was omitted in the antiviral determination in HepG2 cells.

The oligosaccharides associated with the interferon β of the invention may also characterise the interferon β. The interferon β carries oligosaccharides which can be characterised by one or more of the following features:

1. Neutral (no acidic substituents): 5 to 15%, preferably about 10% or lower. Acidic: 95 to 85%, preferably about 90% a or higher.
2. The total desialylated oligosaccharide pool is heterogeneous with at least six distinct structural components present in the pool.
3. Matrix-Assisted Laser Desorption Ionisation—Time of Flight (MALDI-TOF) mass spectrometry and high resolution gel permeation chromatography data are sun as follows:

| Mass detected | Composition | Calculated Mass | gu equivalent |
| --- | --- | --- | --- |
| 1786.2 | 5Hex, 4HexNAc, 1 2AB, Na | 1782 | 11.1 |
| 1929.9 | 5Hex, 1dHex, 4HexNAc, 1 2AB, Na | 1928 | 12.2 |
| 2295.5 | 6Hex, 1dHex, 5HexNAc 1 2AB, Na | 2293 | 14.5 |
| 2660.1 | 7Hex, 1dHex, 6HexNAc 1 2AB, Na | 2658 | 17.6 |
| 3019.1 | 8Hex, 1dHex, 7HexNAc, 1 2AB, Na | 3023 | 20.7 |

The carbohydrate moiety of the human interferon β of WO 96/30531 consist of bi-, tri- and tetra-antennary complex type N-linked oligosaccharides. These oligosaccharides contain repeating lactosamine(s). About 20 to 50%, for example 20 to 30%, 30 to 40% or 35 to 50%, of the oligosaccharides are bi-antennary oligosaccharides. About 30 to 65%, for example from 40 to 60% or 50 to 60%, of the oligosaccharides are tri-antennary oligosaccharides. About 2 to 15%, for example from 2 to 8%, 4 to 10% or 5 to 15%, of the oligosaccharides are tetra-antennary oligosaccharides. Percentages are calculated by weight of total analysable oligosaccharide content.

Inhibitors of the Second Enzyme

Compounds which are inhibitors of inosine monophosphate dehydrogenase, guanosine monophosphate synthetase, cytidine triphosphate synthetase and S-adenosylhomocysteine hydrolase have been reported in WO 00/50064 (the contents of which are incorporated herein by reference) to have anti-viral activity against viruses of the Flaviviridae and Rhabdoviridae families. Examples of these compounds include 5-membered carbocyclic nucleosides and mycophenolic acid compounds such as those described below.

Some of these antiviral compounds have been tested as inhibitors of dihydroorotate dehydrogenase and found to be inactive. This indicates that (a) the replication of flaviviruses, rhabdoviruses and paramyxoviruses in cells involves more than the inhibition of dihydroorotate dehydrogenase, and (b) dihydroorotate dehydrogenase is only one of several nucleotide synthesis enzymes necessary for viral replication.

This finding offers an opportunity for combination therapy whereby infections attributable to viruses of the Flaviviridae, Rhabdoviridae and Paramyxoviridae families may be treated using a dihydroorotate dehydrogenase inhibitor and an inhibitor of a second enzyme selected from guanosine monophosphate dehydrogenase, guanosine monophosphate synthetase, cytidine triphosphate synthetase and S-adenosylhomocysteine hydrolase. If desired the two inhibitors may be used in combination with an interferon. The strategy of using combination therapy addresses the problem of multidrug resistance which typically arises when a single agent is used to treat a disease or disorder.

The 5-membered carbocyclic nucleoside may have the following formula (XI):

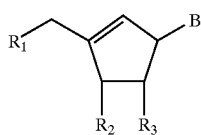
(XI)

wherein B is selected from the group consisting of purines, pyrimidines and five- or six-membered agylcones, $R_2$ and $R_3$ are independently selected from the group consisting of H, halogen, OH, O-acyl, O-aryl and O-silyl, and $R_1$ is as defined for $R_2$ and $R_3$ or is O-phosphate, or a pharmaceutically acceptable metabolite, metabolite derivative or salt thereof.

Preferred compounds of formula (XI) are those in which B denotes one of the following groups (i) to (viii):

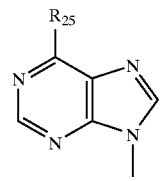
(i)

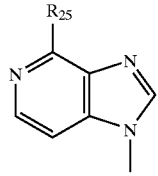
(ii)

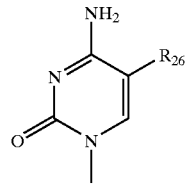
(iii)

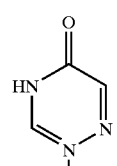
(iv)

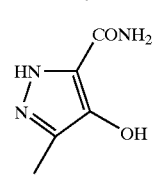
(v)

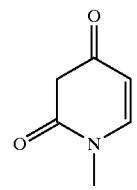
(vi)

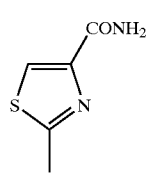
(vii)

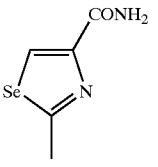
(viii)

wherein $R_{25}$ is Cl or $NH_2$ and $R_{26}$ is H, $CH_3$, $CF_3$, F, Cl, Br or I.

The 5-membered carbocyclic nucleosides of formula (XI) are known compounds and may be synthesised by published procedures or by analogy with published procedures. For instance the synthesis of (−)-neplanocin A is described by Arita et al in *J. Am. Chem. Soc.* (1983), 105 (12), 4049–4055.

The synthesis of other suitable cyclopentenyl carbocyclic nucleosides is described in U.S. Pat. No. 4,975,434, the contents of which are incorporated herein by reference. Specific nucleosides are listed in that patent.

The substitution patterns of preferred compounds of formula (XI) are shown in the Table below. A particularly preferred compound is cyclopentenyl cytidine (CPE-C).
Substitution Patterns within Formula (XI)

| $R_1$ | $R_2$ | $R_3$ | Formula of Nu | Compound |
|---|---|---|---|---|
| OH | OH | OH | (ii) wherein $R_{25}$ is $NH_2$ | 3-deazaneplanocin A |
| OH | OH | OH | (i) wherein $R_{25}$ is $NH_2$ | neplanocin A |
| OH | OH | OH | (iii) wherein $R_{26}$ is H | cyclopentenylcytidine (CPE-C) |

The mycophenolic acid compounds may have the following structure (XII):

(XII)

wherein
$R_4$ is $OR_6$ or —$N(R_7)$ $R_8$ in which $R_6$, $R_7$ and $R_8$ are independently selected from the group consisting of hydrogen and $C_1$–$C_6$ alkyl, and $R_5$ is selected from the group consisting of hydrogen, phenyl and $C_1$–$C_6$ alkyl unsubstituted or substituted by a five- or six-membered saturated or unsaturated heterocyclic rings Preferred compounds of formula (XII) include those in which $R_4$ is hydroxy or $NH_2$. When one or more of $R_5$, $R_6$, $R_7$ and $R_8$ is a $C_1$–$C_6$ alkyl group, preferably it is a $C_1$–$C_4$ alkyl group such as methyl or ethyl. The five- or six-membered saturated or unsaturated heterocyclic ring generally contains one, two or three N-atoms and optionally an O- and/or S-atom. Suitable such rings include pyridino, piperidino, pyrrolo, pyrrolidono and morpholino rings. A N-morpholino ring may thus be present.

Mycophenolic acid compounds suitable for use in the invention in combination with an inhibitor of dihydroorotate dehydrogenase include mycophenolic acid, mycophenolate mofetil which is the morpholinoethyl ester of mycophenolic acid, and the individual mycophenolic acid derivatives described in U.S. Pat. No. 5,380,879. The contents of U.S. Pat. No. 5,380,879 are incorporated herein by reference.

Therapeutic Uses

The dihydroorotate dehydrogenase inhibitors are used to treat flavivirus, rhabdovirus and paramyxovirus infections, particularly in humans. The infection may be acute or chronic. The flavivirus may be yellow fever virus, kunjin virus, West Nile virus, dengue virus, a hepatitis virus such as hepatitis C virus, or an encephalitis virus such as St. Louis encephalitis virus, Japanese encephalitis virus, Murray valley encephalitis virus and tick-borne encephalitis virus. The rhabdovirus may be vesicular stomatis virus or rabies virus. The paramyxovirus may be respiratory syncytial virus (RSV).

A therapeutically effective amount of an inhibitor of dihydroorotate dehydrogenase is administered to a subject to be treated. The condition of the subject can thus be improved. The infection may be cleared from the subject entirely.

The inhibitor can be administered in a variety of dosage forms, for example orally such as in the form of tablets, capsules, sugar- or film-coated tablets, liquid solutions or suspensions or parenterally, for example intramuscularly, intravenously or subcutaneously. It may therefore be given by injection or infusion.

The mode of administration and dosage regimen of the inhibitor depends on a variety of factors including the particular inhibitor concerned, the age, weight and condition of the patient and the nature of the viral infection. Typically, however, the dosage adopted for each route of administration for humans, for example adult humans, is 0.001 to 30 mg/kg, most commonly in the range of 0.01 to 5 mg/kg, body weight. Such a dosage may be given, for example, daily. The dosage may be given orally or by bolus infusion, infusion over several hours and/or repeated administration.

An interferon may also be administered to the subject under treatment. The inhibitor of dihydroorotate dehydrogenase and the interferon may be given simultaneously. Alternatively they may be given up to five days from each other, for example up to two days apart or up to one day apart or up to four hours apart The relative timing of the administration of the inhibitor and the interferon may be determined by monitoring their respective serum levels. The interferon may be given before the inhibitor of dihydroorotate dehydrogenase, or vice versa.

The interferon may be administered in various ways such as orally, intravenously, intramuscularly, intraperitoneally, intranasally, intradermally, and subcutaneously. The particular mode of administration and dosage regimen will be selected by the attending physician taking into account a number of factors including the age, weight and condition of the patient, the nature of the viral infection, the dihydroorotate dehydrogenase inhibitor with which it is being administered and, as required, the need to obtain a synergistic effect.

An inhibitor of a second enzyme selected from inosine monophosphate dehydrogenase, guanosine monophosphate synthetase, cytidine triphosphate synthetase and S-adenosylhomocysteine hydrolase may be administered to the subject under treatment in addition to the inhibitor of dihydroorotate dehydrogenase, either in addition to or instead of the interferon. Suitable dosages and formulations of the inhibitor of the said second enzyme are described in WO 00/50064 mentioned above.

Separate formulations of the inhibitor of dihydroorotate dehydrogenase on the one hand and of the inhibitor of the said second enzyme and/or the interferon on the other hand will generally be given to a patient. A single formulation containing each component can however be administered if the dihydroorotate dehydrogenase inhibitor and the inhibitor of the said second enzyme and/or the interferon are stable in each other's presence and do not otherwise interfere with each other.

The pharmaceutical compositions that contain the interferon as an active principal will normally be formulated with an appropriate pharmaceutically acceptable carrier or diluent depending upon the particular mode of administration being used. For instance, parenteral formulations are usually injectable fluids that use pharmaceutically and physiologically acceptable fluids such as physiological saline, balanced salt solutions, or the like as a vehicle which may contain physiologically acceptable amounts of organic diluents such as DMSO. Oral formulations, on the other hand, may be solids, e.g. tablets or capsules, or liquid solutions or suspensions.

The inhibitor of dihydroorotate dehydrogenase and the interferon, or the inhibitor of dihydroorotate dehydrogenase and the inhibitor of the said second enzyme are typically administered in such amounts that a synergistic effect is obtained. Lower doses of the two inhibitors and of interferon can be used, which results in a cost-saving and a reduction or elimination of side effects that might occur at higher doses. The interferon will usually be formulated as a unit dosage form that contains from $10^4$ to $10^9$, more usually $10^6$ to $10^7$, IU per dose. Typically from $3 \times 10^6$ to $36 \times 10^6$ IU of interferon is administered per day, particularly by injection such as intravenously or subcutaneously. The dosage may be administered daily, for example for up to five or up to twenty weeks.

The following Examples illustrate the invention.

EXAMPLE 1

Test compounds were weighed and freshly dissolved in dimethyl sulfoxide (DMSO). Stock solutions of each chemical in DMSO were kept at 4° C. or for longer storage at minus 80° C. The stock solutions were diluted in regular medium such that the concentrations of each chemical ranged down from 100 $\mu$M as they were serially diluted two times to nM concentrations.

Human liver (HuH7) cells, human primary fibroblats (MRC5) and transformed monkey cells (Vero) cultured in 96 well microtitre plates were each grown to near confluency in regular medium The media was removed and each well of cells was re-incubated with 0.1 ml, of regular medium containing 1 to 2% of fetal calf serum, different concentrations of each of the chemical compounds dissolved in regular medium and an amount of each of the viruses listed in Tables 1 and 2. The controls consisted of cell controls (cells treated with chemical compounds but not with virus) as well as viral controls (cells treated only with virus but not with chemicals). Nearly all the cells (90–100%) in the viral control were in fact killed by the viral challenge after several days of incubation with the virus at 37° C. (1 to 2 days for VSV, 5 to 6 days for yellow fever virus and 7 to 8 days for dengue fever and kunjin viruses). Cell toxicity was assessed by gross morphological changes, cell lysis and/or cell cytopathic effects as monitored with the aid of a microscope 1 to 2, 5 to 6 or 7 to 8 days (to correspond to the number of days, respectively, required for VSV, yellow fever or dengue and kunjin virus to kill the cells) after the cells had been concurrently treated with a given concentration of each compound and the virus.

The results are shown in Tables 1 and 2. The antiviral activity of a compound is indicated by its $ED_{50}$ value which is the concentration of test compound that confers a 50% protection against a 100 TCID50 challenge dose of yellow fever virus, dengue virus or kunjin virus or RSV, or against a challenge virus of vesicular stomatitis virus at an multiciplicity of infection (M.O.I.) of 2.0.

TABLE 1

Antiviral Activities of Test Compounds

| Test compound | $ED_{50}$ ($\mu$M) | Virus Challenge ($TCID_{50}$) | Cell Type | Selectivity Index[A] |
|---|---|---|---|---|
| BNID | 1.25 | yellow fever | Vero | ND |
| | 1.05 | kunjin | Vero | |
| | 1.25 | dengue | Vero | |
| | 1.15 | yellow fever | HuH7 | |
| | 1.15 | kunjin | HuH7 | |
| | 0.64 | VSV | HuH7 | |
| Brequinar | 0.02 | yellow fever | Vero | 2667 |
| | 0.02 | kunjin | Vero | |
| | 0.02 | dengue virus | Vero | |
| | 0.05 | yellow fever | HuH7 | |
| | 0.03 | yellow fever | HuH7 | 60* |
| | 0.03 | kunjin | HuH7 | |
| | 0.014 | VSV | HuH7 | 2095** |
| Dichloroallyl lawsone | 0.90 | yellow fever | Vero | ND |
| | 1.10 | yellow fever | HuH7 | |
| | 0.78 | kunjin | HuH7 | |
| | 0.49 | VSV | HuH7 | |
| Redoxal | 0.25 | yellow fever | Vero | ND |
| | 0.39 | kunjin | Vero | |
| | 0.39 | dengue | Vero | |
| | 0.63 | yellow fever | HuH7 | |
| | 0.52 | kunjin | HuH7 | |
| | 0.63 | VSV | HuH7 | |
| Ribavirin | 205 | yellow fever | Vero | 36 |
| | 309 | kunjin | Vero | |
| | 320 | dengue | Vero | |
| | 34 | yellow fever | HuH7 | 70 |
| | 60 | kunjin | HuH7 | |
| | 120 | VSV | MRC5 | |
| | 250 | VSV | HuH7 | |

[A]Selectivity index (SI) is estimated by the ratio of the cytotoxic dose over $ED_{50}$.
*SI @ 5 days
**SI @ 2 days
ND Not determined

TABLE 2

Antiviral activites of Test compounds

| | | ED50 $\mu$M | | | | | | |
|---|---|---|---|---|---|---|---|---|
| Compound | Mol Wt | VSV MRC5 | VSV HuH7 | YFV HuH7 | KUN HuH7 | YFV VERO | DEN VERO | RSV VERO |
| Brequinar | 375 | NA | 0.08 | 0.03 | 0.04 | 0.02 | 0.04 | 0.02 |
| I3K5 | 343 | NA | 0.03 | 0.03 | 0.03 | 0.2 | 0.1 | 0.02 |
| I3K55 | 357 | NA | NA | 0.1 | 0.08 | 0.1 | 0.2 | |
| I3K46 | 349 | NA | NA | 0.1 | 0.1 | 0.1 | 0.5 | |
| I3K52 | 359 | 100 | NA | 0.3 | 0.2 | 1.7 | NA | |
| I3K53 | 403 | | NA | 0.4 | 0.7 | 0.7 | 12.4 | |
| I1K52 | 341 | NA | NA | 0.5 | 0.5 | 3.7 | 7.3 | |
| I1K46 | 331 | NA | | 1 | 0.8 | 3.8 | 3.8 | |

TABLE 2-continued

Antiviral activites of Test compounds

ED50 µM

| Compound | Mol Wt | VSV MRC5 | VSV HuH7 | YFV HuH7 | KUN HuH7 | YFV VERO | DEN VERO | RSV VERO |
|---|---|---|---|---|---|---|---|---|
| I1K53 | 385 | | NA | 1 | 0.9 | 3.2 | 6.5 | |
| I1K55 | 339 | 168 | 1.9 | 0.5 | 0.2 | | | |
| I2K5 | 409 | NA | NA | 1.7 | 2 | 0.8 | 0.8 | |
| I3K4 | 367 | NA | NA | 2.1 | 3.4 | 0.9 | 0.9 | |
| I3K36 | 335 | NA | NA | 3 | 3.6 | 1.9 | 3.7 | |
| I2K46 | 349 | NA | NA | 5.1 | 6.3 | NA | NA | |
| I2K52 | 425 | NA | NA | 11.3 | 9.6 | NA | NA | |
| I2K55 | 423 | | | 6.1 | 5.8 | 11.8 | 11.8 | |
| I2K51 | 483 | NA | NA | NA | | 1.3 | 2.6 | |
| I3K51 | 417 | 74 | | 3.1 | 2.4 | 6 | 23.9 | |
| I3K44 | 307 | | | 10.7 | 15.5 | 32.4 | | |
| I3K6 | 317 | | | 15 | 13.2 | 7.9 | | |
| I2K42 | 389 | | | | 27.7 | | | |
| I2K43 | 363 | | | 102.9 | 46.5 | | | |
| I3K42 | 323 | | | | 53 | | | |
| I2K20 | 353 | | | | 110.7 | | | |
| I3K43 | 297 | | | 100.9 | 85.1 | | | |
| I1K44 | 289 | | | | 133.9 | | | |

EXAMPLE 2

Vero cells and HuH7 cells were grown to about 99% confluency in 96 microwells with minimum essential medium (MEM) containing 10% fetal calf serum. Growth medium was removed from the microwells and incubated with one of the following:

(1) 100 µl of interferon α8 containing either 6, 3, 0.6, 0.3, 0.06, or 0.03 IU of interferon (Reference to Gb 23-902-531, NIH standard, distributed by the Natl. Inst. Allergy and Infectious Diseases, NIH, USA) per ml of MEM containing 2.5 mg/ml human serum albumin.

(2) 100 µl of interferon α2 containing either 6, 3, 0.6, 0.3, 0.06 or 0.03 IU of interferon (Reference to MRC 69/19 as well as Gb-23-902-531 standards) per ml of MEM containing 2.5 mg/ml hum an serum albumin.

(3) 100 µl of interferon β containing 60, 30, 6, 3 or 0.6 IU of interferon (Reference to Gb23-902-53 1 standard) per ml of MEM containing 2.5 mg/ml human serum albumin.

The experiment was done in quadruplicates or duplicates. After the addition of interferon to the Vero cells in the microwells, 100 µl of a viral challenge consisting of 100 TCLD$_{50}$ yellow fever virus, kunjin virus, dengue virus or VSV was added immediately to each of the microwells. Different concentrations of test compound were included in the viral challenge as well. In the case where no test compound was used (i.e. the viral control), only 100 µl of the viral challenge was added to the wells in 100 µl of MEM containing 2.5 mg/ml human serum albumin. The test compound was Brequinar.

In the control cells treated with test compound alone, 100 µl of MEM containing 2.5 mg/ml human serum albumin instead of interferon was added to the cells followed by an addition of another 100 µl of MEM/human serum albumin (2.5 mg/ml) containing test compound. The cells were examined for virus-induced cytopathic effects on days 1 to 2, 5 to 6 or 7 to 8 (to correspond to the number of days, respectively, required for VSV, yellow fever or dengue and kunjin virus to kill the cells) for the antiviral activities of interferon or of the test compound. The results are shown in Table 3.

TABLE 3

Enhancement of Antiviral Effect of Interferon by Test Compound

| Test Compound | µM of Test Compound | Type of Human Interferon | Challenge Virus | Cell Type | Fold enhancement |
|---|---|---|---|---|---|
| Brequinar | 0.04 | α8 | yellow fever | Vero | 3 |
| | 0.04 | α2 | yellow fever | Vero | 10 |
| | 0.04 | β | yellow fever | Vero | 5 |
| | 0.10 | α8 | yellow fever | Vero | 15 |
| | 0.10 | α2 | yellow fever | Vero | 20 |
| | 0.10 | β | yellow fever | Vero | 20 |
| | 0.10 | α2 | dengue | Vero | 10 |
| | 0.02 | β | kunjin | HuH7 | 4.5 |
| | 0.02 | β | yellow fever | HuH7 | 4.5 |
| | 0.057 | β | VSV | HuH7 | 266 |
| BNID | 1.2 | α8 | yellow fever | Vero | 10 |
| | 1.2 | α2 | yellow fever | Vero | 5 |
| | 1.2 | β | yellow fever | Vero | 5 |
| | 1.2 | β | kunjin | Vero | 6 |
| I2K5 | 0.161 | α2 | yellow fever | Vero | 3 |
| I3K5 | 0.114 | α2 | yellow fever | Vero | 3 |
| | 0.114 | α8 | yellow fever | Vero | 3 |
| | 0.114 | β | yellow fever | Vero | 3 |
| | 0.160 | α2 | yellow fever | Vero | 10 |
| | 0.160 | α8 | yellow fever | Vero | 3 |
| | 0.160 | β | yellow fever | Vero | 3 |
| | 0.224 | α2 | yellow fever | Vero | 10 |
| | 0.224 | α8 | yellow fever | Vero | 10 |
| | 0.224 | β | yellow fever | Vero | 33 |
| | 0.297 | α2 | Dengue | Vero | 10 |
| | 0.297 | β | Dengue | Vero | 3 |
| | 0.417 | α2 | Dengue | Vero | 33 |
| | 0.417 | α8 | Dengue | Vero | 10 |
| | 0.417 | β | Dengue | Vero | 33 |
| | 0.222 | α2 | Kunjin | Vero | 3 |
| | 0.312 | α8 | Kunjin | Vero | 3 |

EXAMPLE 3

Peparation of Novel Compunds of Formula IIa

A mixture of the trifluoromethoxy-substituted isatin of formula (IX) defined above (0.3 mmol) and potassium hydroxide (1.8 mmol in 1 ml of water) was heated at 125°

C. in ethanol (2 mL) for 2 hours. A ketone of formula (X) as defined above in which $R^{22}$, $R^{33}$, $R^{44}$ and $R^{55}$ are all hydrogen (0.6 mmol in 1 mL ethanol) was added and the mixture was refluxed further for 12 hours.

The mixture was cooled and concentrated under reduced pressure. The residue was taken up in water (25 mL) and extracted with diethyl ether (2×20 mL). The aqueous layer was acidified with glacial acetic acid until precipitation occurred. The resulting precipitate of 2-(4-biphenylyl)-6-trifluoromethoxy-quinoline-4-carboxylic acid (compound I2K5) was filtered, washed thoroughly and dried in high vacuum for 2 days.

Characterising data for the compound are as follows: NMR: (Acetone-d6, 400 MHz)) δ:7.42–7.54 (m, 3H), 7.76–7.79 (m, 3H), 7.88(d, J=8.44 Hz, 2H), 8.30 (d, J=9.16 Hz, 1H), 8.44–8.47 (m, 2H), 8.76 (s, 1H), 8.94 (s, 1H). $C_{23}H_{14}F_3NO_3$ calcd. 409.1; found 410.1 $(M+H)^+$.

By the method described above, using the appropriately substituted ketone of formula (X), the following compounds were prepared:

2-(4-biphenylyl)-3-methyl-6-trifluoromethoxy-quinoline-4-carboxylic acid (I2K55); NMR: (Acetone-d6, 400 MHz) δ: 2.44 (s, 3H), 7.49 (t, J=7.31 Hz, 1H)(t, J=7.59 Hz, 2H), 7.62 (d,J=8.57Hz, 1H), 7.72–7.82 (m, 6H), 7.92 (s, 1H), 8.09 (d, J=9.16 Hz, 1H). $C_{24}H_{16}F_3NO_3$ calcd. 423.1; found 424.1 $(M+H)^+$.

2-(4-cyclohexylphenyl)-6-trifluoromethoxy-quinoline-4-carboylic acid (I2K46); NMR: (Acetone-d6, 400 MHz) δ:1.29–1.34 (m, 1H), 1.42–1.58 (m, 4H), 1.75–1.78 (m, 1H), 1.85–1.96 (m, 4H), 2.62–2.68 (m, 1H), 7.46 (d, J=8.20 Hz, 2H), 7.78 (d, J=9.16 Hz, 1H), 8.28–8.31 (m, 3H), 8.69 (s, 1H), 8.91 (s, 1H). $C_3H_{20}F_3NO_3$ calcd. 415.1; found 416.1 $(M+H)^+$.

2-(4-benzyloxy-2-methoxy-3-methyl-phenyl)-6-trifluoromethoxy-quinoline-4-carboxylic acid (I2K51); NMR: (Acetone-d6, 400 MHz) δ: 2.29 (s, 3H), 3.58 (s, 3H), 5.27 (s, 2H), 7.07 (d, J=8.64 Hz, 1H), 7.35 (t, J=7.23 Hz, 1H), 7.43 (t, J=7.48 Hz, 2H), 7.55 (d, J=7.39 Hz, 1H), 7.77 (d, J=8.82 Hz, 1H), 7.87 (d, J=8.73 Hz, 2H), 7.77 (d, J=8.82 Hz, 1H), 7.87 (d, J=8.65 Hz, 1H), 8.27 (d, J=9.15 Hz, 1H), 8.79 (s, 1H, 8.96 (s, 1H), $C_{26}H_{20}F_3NO_5$ calcd. 483.1; found 484.1 $(M+H)^+$; and 2-(4-phenoxyphenyl)-6-trifluoromethoxy-quinoline-4-caboxylic acid (I2K52); NMR: (Acetone-d6, 400 MHz) δ: 7.12–7.21 (m, 5H), 7.43–7.47 (m, 2H), 7.78 (d, J=9.20 Hz, 1H), 8.27 (d, J=9.22 Hz, 1H), 8.39 (d, J=8.89 Hz, 2H), 8.68 (s, 1H), 8.92 (s, 1H). $C_{23}H_{14}F_3NO_4$ calcd. 425.1: found 426.1 $(M+H)^+$.

What is claimed is:

1. A method of treating a host infected with a virus of the Flaviviridae, Rhabdoviridae or Paramyxoviridae family, which method comprises administering to the host an inhibitor of dihydroorotate dehydrogenase, wherein the inhibitor is a compound of the formula (I):

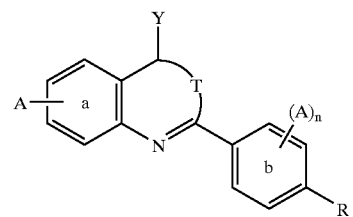

(I)

wherein
each A is independently selected from the group consisting of hydrogen, hydroxy, halogen, perhaloalkoxy, amino $C_1$–$C_8$ alkyl, $NO_2$, CN, $SO_2CH_3$, $C_1$–$C_8$ alkyl, $C_1$–$C_8$ alkoxy, $C_3$–$C_7$ cycloalkyl, $C_3$–$C_7$ cycloalkenyl, aryl, aryloxy, $C_1$–$C_6$ perhaloalkyl and Y; or two adjacent groups A on ring b form, together with the phenyl ring to which they are attached, a naphthalene ring system;

R is cyclohexyl, phenoxy or benzoxy, or a phenyl ring which is unsubstituted or substituted by a group A as defined above; or R and an adjacent group A on ring b form, together with the phenyl ring to which they are attached, a naphthalene or phenanthrene ring system; Y is selected from the group consisting of COOM, CONHR', $SO_3M$ and hydrogen;

M is selected from the group consisting of H, Li, Na, K and 0.5 Ca;

R' is $C_1$–$C_{10}$ alkyl;

n is 1 or 2; and

T is =N or =C(Z) wherein either:
  (i) Z is selected from the group consisting of hydrogen, $NH_2$, OH, $C_1$–$C_8$ alkyl, $C_3$–$C_7$ cycloalkyl, aryl and $C_1$–$C_6$ perhaloalkyl, or
  (ii) Z is a bridging moiety selected from the group consisting of —V—W— (wherein V is $CH_2$ or S and W is $CH_2$, O, S or NH) and —$(CH_2)_2$—C(=Z)— wherein Z is O or $H_2$, the said bridging moiety being attached to the ortho position of ring b of the adjacent biphenyl group, thereby completing a ring.

2. A method according to claim 1, wherein the inhibitor is a compound of formula (Ia):

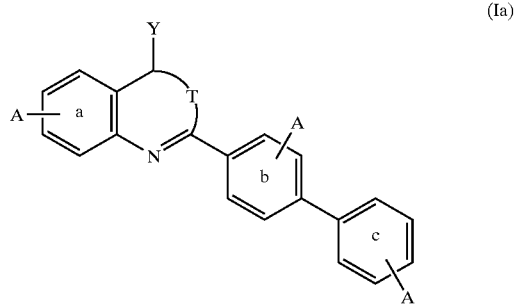

(Ia)

wherein:
each A is independently selected from the group consisting of hydrogen, halogen, amino $C_1$–$C_8$ alkyl, $NO_2$, CN, $SO_2CH_3$, $C_1$–$C_8$ alkyl, $C_3$–$C_7$ cycloalkyl, aryl, $C_1$–$C_6$ perhaloalkyl and Y;

Y is selected from the group consisting of COOM, CONHR' $SO_3M$ and hydrogen;

M is selected from the group consisting of H, Li, Na, K and 0.5 Ca;

R' is $C_1$–$C_{10}$ alkyl; and

T is =N— or =C(Z)— wherein either:
(i) Z is selected from the group consisting of hydrogen, $NH_2$, OH, $C_1$–$C_8$ alkyl, $C_3$–$C_7$ cycloalkyl, aryl and $C_1$–$C_6$ perhaloalkyl, or
(ii) Z is a bridging moiety selected from the group consisting of —V—W— (wherein V is $CH_2$ or S and W is $CH_2$, O, S or NH) and —$(CH_2)_2$—C(=Z)— wherein Z is O or $H_2$, the said bridging moiety being attached to the ortho position of ring b of the adjacent biphenyl group, thereby completing a ring.

3. A method according to claim 1, wherein the inhibitor is a compound of the formula (II):

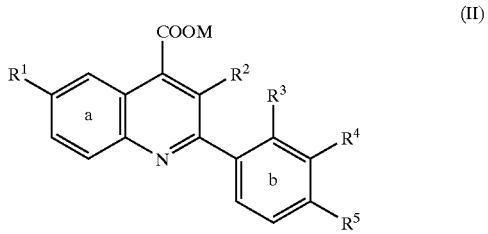

(II)

wherein $R^1$ is H, a halogen or $OCF_3$;

$R^2$ is H or $C_1$–$C_6$ alkyl;

$R^3$ is H or $OR^6$ wherein $R^6$ is H or $C_1$–$C_6$ alkyl;

$R^4$ is H or $C_1$–$C_6$ alkyl; or $R^4$ and $R^3$ form, together with phenyl ring b to which they are attached, a naphthalene ring; and $R^5$ is cyclohexyl, phenoxy or benzoxy, or a phenyl ring which is unsubstituted or substituted by halogen; or $R^4$ and $R^5$ form, together with phenyl ring b to which they are attached, a phenanthrene ring.

4. A method according to claim 3, wherein the inhibitor is a compound of formula (IIb):

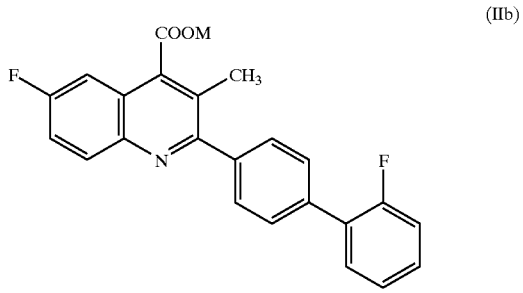

(IIb)

wherein M is H or Na.

5. A method according to claim 1, wherein the virus is a flavivirus selected from the group consisting of hepatitis viruses, yellow fever virus, West Nile virus, kunjin virus, dengue virus, St. Louis encephalitis virus, Japanese encephalitis virus, Murray valley encephalitis virus and tick-borne encephalitis virus.

6. A method according to claim 1, wherein the virus is a rhabdovirus selected from vesicular stomatitis virus and rabies virus, or is the paramyxovirus RSV.

7. A method according to claim 1, wherein the method comprises administration of the inhibitor of formula (I) with an interferon.

8. A method according to claim 7, wherein the interferon is a human interferon.

9. A method according to claim 7, wherein the interferon is selected from the group consisting of interferon α2, interferon α8, and interferon β.

10. A method according to claim 7, wherein the interferon is human interferon α8 having a specific activity of from $0.3 \times 10^9$ to $3 \times 10^9$ IU per mg protein.

11. A method according to claim 7, wherein the interferon is human interferon β having a specific activity of from $2 \times 10^8$ to $8 \times 10^8$ per mg protein.

12. A method according to claim 7, wherein the inhibitor and the interferon are used in respective amounts which produce a synergistic effect.

13. A method according to claim 1, wherein the method further comprises administration of an inhibitor of a second enzyme, which enzyme is selected from inosine monophosphate dehydrogenase, guanosine monophosphate synthetase, cytidine triphosphate synthetase and S-adenosylhomocysteine hydrolase.

14. A method according to claim 13, wherein the inhibitor of the second enzyme is mycophenolic acid, cyclopentenyl cytosine (CPE-C) or 3-deazaneplanocin A.

15. A method according to claim 13, wherein the inhibitor of the second enzyme and the inhibitor of dihydrooratate dehydrogenase are used in respective amounts which produce a synergistic effect.

16. A method according to claim 14, wherein the inhibitor of the second enzyme and the inhibitor of dihydrooratate dehydrogenase are used in respective amounts which produce a synergistic effect.

17. A compound of formula (IIa):

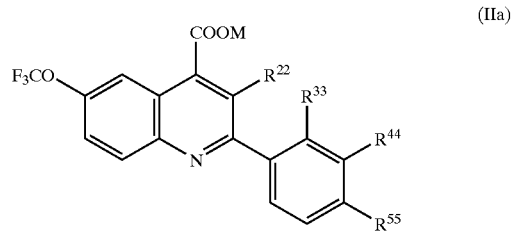

(IIa)

wherein

M is selected from the group consisting of H, Li, Na, K and 0.5 Ca;

$R^{22}$ is H or $C_1$–$C_6$ alkyl;

$R^{33}$ is H or $OR^6$ wherein $R^6$ is H or $C_1$–$C_6$ alkyl;

$R^{44}$ is H or $C_1$–$C_6$ alkyl; and $R^{55}$ is phenyl, cyclohexyl, phenoxy or benzoxy;

or a metabolite or prodrug precursor thereof.

18. A compound according to claim 17, which is selected from:
2-(4-biphenylyl)-6-trifluoromethoxy-quinoline-4-carboxylic acid (compound I2K5);
2-(4-biphenylyl)-3-methyl-6-trifluoromethoxy-quinoline-4-carboxylic acid (compound I2K55);
2-(4-cyclohexylphenyl)-6-trifluoromethoxy-quinoline-4-carboxylic acid (compound I2K46);
2-(4-benzyloxy-2-methoxy-3-methyl-phenyl)-6-trifluoromethoxy-quinoline-4-carboxylic acid (compound I2K51); and
2-(4-phenoxyphenyl)-6-trifluoromethoxy-quinoline-4-carboxylic acid (compound I2K52).

19. A process for producing a compound of formula (IIa) as claimed in claim 17, which process comprises a) condensing a trifluoromethoxy-substituted isatin compound of the following formula (IX):

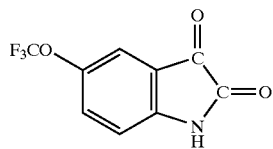

(IX)

with a ketone of formula (X):

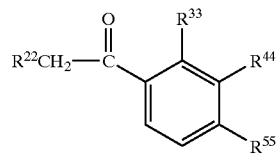

(X)

in the presence of a base; and (b) if desired, converting a resulting compound of formula (IIa) in which M is H into a pharmaceutically acceptable salt thereof wherein M is Li, Na, K or 0.5 Ca.

20. An anti-flavivirus, anti-rhabdovirus or anti-paramyxovirus agent comprising an inhibitor of dihydro-orotate dehydrogenase which is a compound of formula (IIa):

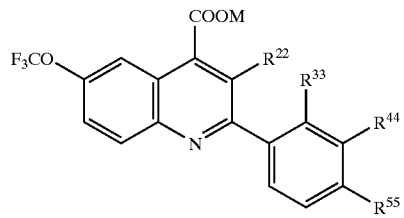

(IIa)

wherein

M is selected from the group consisting of H, Li, Na, K and 0.5 Ca;

$R^{22}$ is H or $C_1$–$C_6$ alkyl;

$R^{33}$ is H or $OR^6$ wherein $R^6$ is H or $C_1$–$C_6$ alkyl;

$R^{44}$ is H or $C_1$–$C_6$ alkyl; and $R^{55}$ is phenyl, cyclohexyl, phenoxy or benzoxy;

or a metabolite or prodrug precursor thereof.

21. An anti-flavivirus, anti-rhabdovirus or anti-paramyxovirus agent according to claim 20, which further comprises an interferon.

22. An anti-flavivirus, anti-rhabdovirus or anti-paramyxovirus agent according to claim 20, further comprising an inhibitor of a second enzyme, which enzyme is selected from inosine monophosphate dehydrogenase, guanosine monophosphate synthetase, cytidine triphosphate synthetase and S-adenosylhomocystein hydrolase.

23. An anti-flavivirus, anti-rhabdovirus or anti-paramyxovirus agent according to claim 22, which further comprises an interferon.

* * * * *